US010314773B2

(12) United States Patent
Nicou et al.

(10) Patent No.: US 10,314,773 B2
(45) Date of Patent: *Jun. 11, 2019

(54) DYE COMPOSITION COMPRISING A PARA-PHENYLENEDIAMINE OXIDATION BASE, A NONIONIC SURFACTANT IN A MEDIUM RICH IN FATTY SUBSTANCES

(71) Applicant: L'OREAL, Paris (FR)

(72) Inventors: Valerie Nicou, Clichy (FR); Isabelle Rollat, Paris (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/537,016

(22) PCT Filed: Dec. 17, 2015

(86) PCT No.: PCT/EP2015/080370
§ 371 (c)(1),
(2) Date: Jun. 16, 2017

(87) PCT Pub. No.: WO2016/097226
PCT Pub. Date: Jun. 23, 2016

(65) Prior Publication Data
US 2017/0340536 A1 Nov. 30, 2017

(30) Foreign Application Priority Data
Dec. 17, 2014 (FR) .................... 14 62621

(51) Int. Cl.
A61Q 5/10 (2006.01)
A61K 8/34 (2006.01)
A61K 8/31 (2006.01)
A61K 8/41 (2006.01)
A61K 8/60 (2006.01)
A61K 8/86 (2006.01)
A61K 8/39 (2006.01)
A61K 8/49 (2006.01)

(52) U.S. Cl.
CPC ............. A61K 8/342 (2013.01); A61K 8/31 (2013.01); A61K 8/39 (2013.01); A61K 8/41 (2013.01); A61K 8/411 (2013.01); A61K 8/415 (2013.01); A61K 8/4973 (2013.01); A61K 8/604 (2013.01); A61K 8/86 (2013.01); A61Q 5/10 (2013.01); A61K 2800/882 (2013.01)

(58) Field of Classification Search
CPC ........ A61Q 5/10; A61K 8/342; A61K 8/4973; A61K 8/604; A61K 8/39; A61K 8/415; A61K 8/411; A61K 8/41; A61K 2800/882
See application file for complete search history.

(56) References Cited

U.S. PATENT DOCUMENTS

| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 3,206,462 A | 9/1965 | McCarty |
| 3,836,537 A | 9/1974 | Boerwinkle et al. |
| 3,874,870 A | 4/1975 | Green et al. |
| 3,910,862 A | 10/1975 | Barabas et al. |
| 3,912,808 A | 10/1975 | Sokol |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,003,699 A | 1/1977 | Rose et al. |
| 4,005,193 A | 1/1977 | Green et al. |
| 4,025,617 A | 5/1977 | Green et al. |
| 4,025,627 A | 5/1977 | Green et al. |
| 4,025,653 A | 5/1977 | Green et al. |

(Continued)

FOREIGN PATENT DOCUMENTS

| DE | 2359399 A1 | 6/1975 |
| DE | 3843892 A1 | 6/1990 |

(Continued)

OTHER PUBLICATIONS

International Search Report for PCT/EP2015/079434, dated Feb. 1, 2016.
International Search Report for PCT/EP2015/080051, dated Mar. 9, 2016.
International Search Report for PCT/EP2015/079432, dated Mar. 16, 2016.
International Search Report for PCT/EP2015/080370, dated Mar. 14, 2016.
International Search Report for PCT/EP2015/080371, dated Mar. 24, 2016.
International Search Report for PCT/EP2015/080372, dated May 3, 2016.

(Continued)

Primary Examiner — Eisa B Elhilo
(74) Attorney, Agent, or Firm — The Marbury Law Group, PLLC

(57) ABSTRACT

The present invention relates to a composition for dyeing keratin fibers, in particular keratin fibers such as the hair, comprising: a) at least one oxidation base 3-(2,5-diaminophenyl)-1-propanol and/or acid salts thereof or solvates thereof such as hydrates; b) at least one coupler; c) at least 10% by weight of the total weight of the composition of a fatty substance which is preferably liquid and non-silicone-based; d) at least one nonionic surfactant chosen from alkyl(poly)glycoside surfactants, esters of oxyalkylenated sorbitan and fatty acids and oxyalkylenated fatty alcohols; e) optionally at least one basifying agent; and f) optionally at least one chemical oxidizing agent. The invention also relates to a process for dyeing keratin fibers such as the hair using the composition of the invention, and to a multi-compartment device for using the composition of the invention.

21 Claims, No Drawings

(56) References Cited

U.S. PATENT DOCUMENTS

| | | | |
|---|---|---|---|
| 4,026,945 A | 5/1977 | Green et al. | |
| 4,027,008 A | 5/1977 | Sokol | |
| 4,027,020 A | 5/1977 | Green et al. | |
| 4,075,136 A | 2/1978 | Schaper | |
| 4,131,576 A | 12/1978 | Iovine et al. | |
| 4,165,367 A | 8/1979 | Chakrabarti | |
| 4,166,894 A | 9/1979 | Schaper | |
| RE30,199 E | 1/1980 | Rose et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,240,450 A | 12/1980 | Grollier et al. | |
| 4,348,202 A | 9/1982 | Grollier et al. | |
| 4,349,532 A | 9/1982 | Vanlerberghe et al. | |
| 4,381,919 A | 5/1983 | Jacquet et al. | |
| 4,422,853 A | 12/1983 | Jacquet et al. | |
| 4,445,521 A | 5/1984 | Grollier et al. | |
| 4,608,250 A | 8/1986 | Jacquet et al. | |
| 4,719,099 A | 1/1988 | Grollier et al. | |
| 4,839,166 A | 6/1989 | Grollier et al. | |
| 4,840,639 A | 6/1989 | Husemeyer et al. | |
| 4,996,059 A | 2/1991 | Grollier et al. | |
| 5,009,880 A | 4/1991 | Grollier et al. | |
| 5,061,289 A | 10/1991 | Clausen et al. | |
| 5,089,252 A | 2/1992 | Grollier et al. | |
| 5,380,340 A | 1/1995 | Neunhoeffer et al. | |
| 5,457,200 A | 10/1995 | Zimmermann et al. | |
| 5,534,267 A | 7/1996 | Neunhoeffer et al. | |
| 5,616,150 A | 4/1997 | Moeller et al. | |
| 5,663,366 A | 9/1997 | Neunhoeffer et al. | |
| 5,766,576 A | 6/1998 | Lowe et al. | |
| 5,928,385 A | 7/1999 | Cotteret et al. | |
| 5,958,392 A | 9/1999 | Grollier et al. | |
| 6,099,592 A | 8/2000 | Vidal et al. | |
| 6,284,003 B1 | 9/2001 | Rose et al. | |
| 6,338,741 B1 | 1/2002 | Vidal et al. | |
| 6,342,079 B1 | 1/2002 | Pan et al. | |
| 6,503,282 B1 * | 1/2003 | Braun | A61K 8/411 564/443 |
| 6,645,258 B2 | 11/2003 | Vidal et al. | |
| 6,730,789 B1 | 5/2004 | Birault et al. | |
| 3,066,781 A1 | 11/2011 | Hercouet et al. | |
| 2002/0010970 A1 | 1/2002 | Collard et al. | |
| 2002/0046431 A1 * | 4/2002 | Laurent | A61K 8/345 8/405 |
| 2010/0154136 A1 | 6/2010 | Hercouet et al. | |
| 2011/0158925 A1 | 6/2011 | Ascione et al. | |
| 2013/0048007 A1 | 2/2013 | Fadli | |
| 2014/0137342 A1 * | 5/2014 | Guerin | A61K 8/4926 8/405 |
| 2014/0318566 A1 | 10/2014 | Mignon et al. | |
| 2015/0082554 A1 | 3/2015 | Allard et al. | |
| 2015/0202142 A1 | 7/2015 | Charrier et al. | |
| 2015/0335563 A1 | 11/2015 | Allard et al. | |

FOREIGN PATENT DOCUMENTS

| | | |
|---|---|---|
| DE | 4133957 A1 | 4/1993 |
| DE | 19543988 A1 | 5/1997 |
| EP | 0007537 A1 | 2/1980 |
| EP | 0080976 A1 | 6/1983 |
| EP | 0122324 A1 | 10/1984 |
| EP | 0337354 A1 | 10/1989 |
| EP | 0770375 A1 | 5/1997 |
| EP | 1166749 A2 | 1/2002 |
| EP | 2198929 A1 | 6/2010 |
| EP | 2338463 A1 | 6/2011 |
| FR | 1400366 A | 5/1965 |
| FR | 2077143 A5 | 10/1971 |
| FR | 2080759 A1 | 11/1971 |
| FR | 2190406 A2 | 2/1974 |
| FR | 2270846 A1 | 12/1975 |
| FR | 2316271 A1 | 1/1977 |
| FR | 2320330 A1 | 3/1977 |
| FR | 2336434 A1 | 7/1977 |
| FR | 2383660 A1 | 10/1978 |
| FR | 2393573 A1 | 1/1979 |
| FR | 2413907 A1 | 8/1979 |
| FR | 2470596 A1 | 6/1981 |
| FR | 2519863 A1 | 7/1983 |
| FR | 2598611 A1 | 11/1987 |
| FR | 2733749 A1 | 11/1996 |
| FR | 2801308 A1 | 5/2001 |
| FR | 2886136 A1 | 12/2006 |
| FR | 2988591 A1 | 10/2013 |
| FR | 2988594 A1 | 10/2013 |
| FR | 2988595 A1 | 10/2013 |
| FR | 2988598 A1 | 10/2013 |
| FR | 2994085 A1 | 2/2014 |
| GB | 1021400 A | 3/1966 |
| GB | 1026978 A | 4/1966 |
| GB | 1153196 A | 5/1969 |
| GB | 1546809 A | 5/1979 |
| JP | 02-019576 A | 1/1990 |
| JP | 05-163124 A | 6/1993 |
| WO | 80/00214 A1 | 2/1980 |
| WO | 94/08969 A1 | 4/1994 |
| WO | 94/08970 A1 | 4/1994 |
| WO | 94/24988 A1 | 11/1994 |
| WO | 96/15765 A1 | 5/1996 |
| WO | 01/51019 A1 | 7/2001 |
| WO | 2012/080288 A1 | 6/2012 |
| WO | 2012/080289 A2 | 6/2012 |
| WO | 2012/080321 A2 | 6/2012 |
| WO | 2013/144260 A2 | 10/2013 |
| WO | 2013/152956 A2 | 10/2013 |
| WO | 2014/020148 A1 | 2/2014 |
| WO | 2016/096654 A1 | 6/2016 |
| WO | 2016/096655 A1 | 6/2016 |
| WO | 2016/097022 A1 | 6/2016 |
| WO | 2016/097227 A1 | 6/2016 |
| WO | 2016/097228 A1 | 6/2016 |
| WO | 2016/097229 A1 | 6/2016 |

OTHER PUBLICATIONS

International Search Report for PCT/EP2015/080373, dated Feb. 9, 2016.
Non-Final Office Action for co-pending U.S. Appl. No. 15/537,029, dated Oct. 2, 2017.
Non-Final Office Action for co-pending U.S. Appl. No. 15/537,041, dated Oct. 2, 2017.
Non-Final Office Action for co-pending U.S. Appl. No. 15/537,060, dated Sep. 29, 2017.
Non-Final Office Action for co-pending U.S. Appl. No. 15/536,998, dated Sep. 29, 2017.
Final Office Action for copending U.S. Appl. No. 15/537,060, dated May 1, 2018.
Final Office Action for copending U.S. Appl. No. 15/537,029, dated Apr. 17, 2018.
Final Office Action for copending U.S. Appl. No. 15/536,998, dated May 14, 2018.
Non-Final Office Action for copending U.S. Appl. No. 15/537,225, dated Jul. 10, 2018.
Final Office Action for copending U.S. Appl. No. 15/537,041, dated May 18, 2018.
Notice of Allowance for copending U.S. Appl. No. 15/537,029, dated Aug. 1, 2018.
Notice of Allowance for copending U.S. Appl. No. 15/537,029, dated Sep. 20, 2018.
Notice of Allowance for copending U.S. Appl. No. 15/537,060, dated Sep. 17, 2018.
Final Office Action for copending U.S. Appl. No. 15/537,225, dated Nov. 21, 2018.

* cited by examiner

DYE COMPOSITION COMPRISING A PARA-PHENYLENEDIAMINE OXIDATION BASE, A NONIONIC SURFACTANT IN A MEDIUM RICH IN FATTY SUBSTANCES

CROSS REFERENCE TO RELATED APPLICATIONS

This is a national stage application of PCT/EP2015/080370, filed internationally on Dec. 17, 2015, which claims priority to French Application No. 1462621, filed on Dec. 17, 2014, both of which are incorporated by reference herein in their entireties.

The present invention relates to a composition for dyeing keratin fibres using a specific para-phenylenediamine oxidation base, a specific nonionic surfactant and at least 10% of fatty substances.

Many people have sought for a long time to modify the colour of their hair and in particular to hide their grey hair.

One of the dyeing methods is "permanent" or oxidation dyeing, which uses dye compositions containing oxidation dye precursors, generally known as oxidation bases. These oxidation bases are colourless or weakly coloured compounds, which, when combined with oxidizing products, may give rise to coloured compounds via a process of oxidative condensation.

It is also known that the shades obtained with these oxidation bases may be varied by combining them with couplers or colouring modifiers, the latter being chosen especially from aromatic meta-diamines, meta-aminophenols, meta-diphenols and certain heterocyclic compounds such as indole compounds. The variety of the molecules used as oxidation bases and couplers allows a wide range of colours to be obtained.

Permanent dyeing processes thus consist in using, with the composition containing the dye precursors, an aqueous composition comprising at least one oxidizing agent, under alkaline pH conditions in the vast majority of cases. The role of this oxidizing agent is to at least partly degrade the melanin of the hair, which, depending on the nature of the oxidizing agent present, leads to more or less pronounced lightening of the fibres. The oxidizing agent used is generally hydrogen peroxide.

The basifying agent makes it possible to adjust the pH of the composition to an alkaline pH to enable activation of the oxidizing agent. In addition, this basifying agent causes swelling of the keratin fibre, with raising of the scales, which promotes the penetration of the oxidizing agent, and also of the dyes, if they are present, essentially oxidation dyes, into the fibre, and thus increases the efficacy of the dyeing or lightening reaction.

In the long term, the use of an oxidizing agent and an alkaline agent may lead to degradation of the keratin fibres and also to inconvenience at the time of use; in particular, ammonia may give rise to inconvenience to the user due to its strong characteristic odour.

Moreover, not only may the user be inconvenienced by the odour, but he may also be confronted with greater risks of intolerance, for instance irritation of the scalp, which is especially reflected by stinging.

It is also important to obtain intense colouring, which is resistant to external factors such as light, shampoos and sweat, and which is as uniform as possible along the entire fibre, irrespective of the level of damage of the keratin fibre.

Oxidation bases of the para-phenylenediamine type are commonly used in the field of hair dyeing. It is known practice, for example, to use 3-(2,5-diaminophenyl)-1-propanol (or 2-γ-hydroxypropyl-para-phenylenediamine) in oxidation dyeing, especially in document WO 80/00214. However, the dye compositions obtained using this oxidation base are not always satisfactory especially for ensuring suitable coverage of grey hair with an acceptable colouring selectivity between the root and the end and/or sufficient fastness with respect to external attacking factors such as light, shampoos, bad weather, etc.

One of the objects of the present invention is to propose compositions for dyeing human keratin fibres such as the hair, which have superior dyeing properties relative to the existing compositions.

In particular, the composition according to the invention in the presence of a chemical oxidizing agent must make it possible to obtain colours that are satisfactory, especially in terms of power, but also with sufficient uniformity of the colour from the end to the root of the hair, which makes it possible to avoid a "root" effect of the colouring. Finally, it is also possible to obtain colourings that are very stable towards external agents.

Furthermore, the invention makes it possible to achieve substantial degrees of lightening while at the same time colouring, and does so without using oxidizing agents such as persalts or increasing the amount of chemical oxidizing agent or of basifying agent.

Moreover, the composition of the invention makes it possible to obtain formulations that are less malodorous during their application to the hair or during their preparation.

These aims and others are achieved by the present invention, one subject of which is thus a composition for dyeing keratin fibres, in particular human keratin fibres such as the hair, comprising:

a) at least one oxidation base 3-(2,5-diaminophenyl)-1-propanol and/or acid salts thereof and/or solvates thereof such as hydrates;
b) at least one coupler;
c) at least 10% by weight of the total weight of the composition of a fatty substance which is preferably liquid and non-silicone-based;
d) at least one nonionic surfactant chosen from alkyl (poly)glycoside surfactants, esters of oxyalkylenated sorbitan and fatty acids and oxyalkylenated fatty alcohols;
e) optionally at least one basifying agent; and
f) optionally at least one chemical oxidizing agent.

A subject of the invention is also a process for dyeing keratin fibres such as the hair using the composition of the invention, and a multi-compartment device for using the composition of the invention.

Furthermore, the processes according to the invention use formulations that are less malodorous during their application to the hair or during their preparation.

Other characteristics and advantages of the invention will emerge more clearly on reading the description and the examples that follow.

In the text hereinbelow, and unless otherwise indicated, the limits of a range of values are included within that range. The expression "at least one" is equivalent to the expression "one or more".

a) Fatty Substances

As has already been mentioned, the composition of the invention comprises a) one or more fatty substances.

The term "fatty substance" means an organic compound that is insoluble in water at ordinary temperature (25° C.) and at atmospheric pressure (760 mmHg) (solubility of less than 5%, preferably less than 1% and even more preferentially less than 0.1%). They bear in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

Preferably, the fatty substances of the invention do not contain any salified or unsalified carboxylic acid groups (—C(O)OH or —C(O)O⁻). The fatty substances of the invention are neither polyoxyalkylenated nor polyglycerolated.

Preferably, the fatty substances used in the composition according to the invention are non-silicone oils.

The term "oil" means a "fatty substance" that is liquid at room temperature (25° C.) and at atmospheric pressure (760 mmHg).

The term "non-silicone oil" means an oil not containing any silicon atoms (Si) and the term "silicone oil" means an oil containing at least one silicon atom.

More particularly, the fatty substances are chosen from $C_6$-$C_{16}$ hydrocarbons, hydrocarbons containing more than 16 carbon atoms, non-silicone oils of animal origin, plant oils of triglyceride type, synthetic triglycerides, fluoro oils, fatty alcohols, esters of fatty acids and/or of fatty alcohols other than triglycerides, and plant waxes, non-silicone waxes and silicones.

It is recalled that, for the purposes of the invention, the fatty alcohols, fatty esters and fatty acids more particularly contain one or more linear or branched, saturated or unsaturated hydrocarbon-based groups comprising 6 to 30 carbon atoms, which are optionally substituted, in particular, with one or more (in particular 1 to 4) hydroxyl groups. If they are unsaturated, these compounds may comprise one to three conjugated or unconjugated carbon-carbon double bonds.

As regards the $C_6$-$C_{16}$ hydrocarbons, they are linear, branched or optionally cyclic, and are preferably alkanes. Examples that may be mentioned include hexane, dodecane and isoparaffins such as isohexadecane and isodecane.

A hydrocarbon-based oil of animal origin that may be mentioned is perhydrosqualene.

The triglyceride oils of plant or synthetic origin are preferably chosen from liquid fatty acid triglycerides containing from 6 to 30 carbon atoms, for instance heptanoic or octanoic acid triglycerides, or alternatively, for example, sunflower oil, corn oil, soybean oil, pumpkin oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® 810, 812 and 818 by the company Dynamit Nobel, jojoba oil and shea butter oil.

The linear or branched hydrocarbons of mineral or synthetic origin containing more than 16 carbon atoms are preferably chosen from liquid paraffins, petroleum jelly, liquid petroleum jelly, polydecenes and hydrogenated polyisobutene such as Parleam®.

The fluoro oils may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or alternatively bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used in the composition according to the invention are saturated or unsaturated, and linear or branched, and comprise from 6 to 30 carbon atoms and more particularly from 8 to 30 carbon atoms. Mention may be made, for example, of cetyl alcohol, stearyl alcohol and a mixture thereof (cetearyl alcohol), octyldodecanol, 2-butyloctanol, 2-hexyldecanol, 2-undecylpentadecanol, oleyl alcohol or linoleyl alcohol.

The wax(es) that may be used in the composition according to the invention are chosen especially from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant blossom sold by the company Bertin (France), animal waxes, for instance beeswaxes, or modified beeswaxes (cerabellina); other waxes or waxy starting materials that may be used according to the invention are especially marine waxes such as the product sold by the company Sophim under the reference M82, and polyethylene waxes or polyolefin waxes in general.

As regards the fatty acid and/or fatty alcohol esters, which are advantageously different from the triglycerides mentioned above, mention may be made in particular of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisostearyl citrate; glyceryl trilactate; glyceryl trioctanoate; trioctyldodecyl citrate; trioleyl citrate, propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds bearing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this alternative form can also be chosen from mono-, di-, tri- and tetraesters and polyesters, and mixtures thereof.

These esters may be, for example, oleates, laurates, palmitates, myristates, behenates, cocoates, stearates, linoleates, linolenates, caprates or arachidonates, or mixtures thereof such as, in particular, oleate/palmitate, oleate/stearate or palmitate/stearate mixed esters.

More particularly, use is made of mono- and diesters and in particular mono- or di-oleate, -stearate, -behenate, -oleate/palmitate, -linoleate, -linolenate or -oleate/stearate of sucrose, glucose or methylglucose. An example that may be mentioned is the product sold under the name Glucate® DO by the company Amerchol, which is a methylglucose dioleate.

Examples of sugar esters or mixtures of sugar esters of fatty acids that may also be mentioned include:
the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
the products sold under the name Ryoto Sugar Esters, for example referenced B370 and corresponding to sucrose behenate formed from 20% monoester and 80% di-triester-polyester;
the sucrose monopalmitostearate-dipalmitostearate sold by the company Goldschmidt under the name Tegosoft® PSE.

The silicones that may be used in accordance with the invention may be in the form of oils, waxes, resins or gums.

Preferably, the silicone is chosen from polydialkylsiloxanes, in particular polydimethylsiloxanes (PDMSs), and organomodified polysiloxanes comprising at least one functional group chosen from amino groups, aryl groups and alkoxy groups.

Organopolysiloxanes are defined in greater detail in Walter Noll's *Chemistry and Technology of Silicones* (1968), Academic Press. They may be volatile or non-volatile.

These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a nonlimiting manner, of the following commercial products:
the Silbione® oils of the 47 and 70 047 series or the Mirasil® oils sold by Rhodia, for instance the oil 70 047 V 500 000;
the oils of the Mirasil® series sold by the company Rhodia;
the oils of the 200 series from the company Dow Corning, such as DC200 with a viscosity of 60 000 $mm^2$/s;
the Viscasil® oils from General Electric and certain oils of the SF series (SF 96, SF 18) from General Electric.

Mention may also be made of polydimethylsiloxanes having dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The organomodified silicones that may be used in accordance with the invention are silicones as defined previously and comprising in their structure one or more organofunctional groups attached via a hydrocarbon-based group.

The organomodified silicones may be polydiarylsiloxanes, in particular polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ $m^2$/s at 25° C.

Among these polyalkylarylsiloxanes, examples that may be mentioned include the products sold under the following names:
the Silbione® oils of the 70 641 series from Rhodia;
oils of the Rhodorsil® 70 633 and 763 series from Rhodia; the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

Among the organomodified silicones, mention may also be made of polyorganosiloxanes comprising:
substituted or unsubstituted amino groups, such as the products sold under the names GP 4 Silicone Fluid and GP 7100 by the company Genesee or the products sold under the names Q2 8220 and Dow Corning 929 or 939 by the company Dow Corning. The substituted amino groups are, in particular, $C_1$-$C_4$ aminoalkyl groups;
alkoxy groups such as the product sold under the name Silicone Copolymer F-755 by SWS Silicones, and Abil Wax® 2428, 2434 and 2440 by the company Goldschmidt.

Preferably, the fatty substances according to the invention are non-silicone.

The fatty substances are advantageously chosen from $C_6$-$C_{16}$ hydrocarbons, hydrocarbons containing more than 16 carbon atoms, triglycerides, fatty alcohols, esters of fatty acids and/or of fatty alcohols other than triglycerides, or mixtures thereof, which are preferably liquid.

Preferably, the fatty substance(s) are chosen from liquid petroleum jelly, polydecenes, liquid fatty alcohols, liquid esters of fatty acids and/or of fatty alcohols, or mixtures thereof.

Even more preferentially, the fatty substances are chosen from liquid petroleum jelly and octyldodecanol.

According to a particular embodiment, the composition according to the invention comprises at least 10% by weight of fatty substances which are preferably non-silicone, in particular non-silicone oils, relative to the total weight of the composition of the invention. More particularly, the composition according to the invention comprises at least 25% by weight of fatty substances, which are preferably non-silicone, in particular non-silicone oils, relative to the total weight of the composition.

The composition according to the invention more particularly has a fatty substance content ranging from 15% to 80% by weight, preferably from 25% to 75% by weight, better still from 30% to 70% by weight and even more advantageously from 30% to 60% by weight relative to the weight of the composition.

According to a particular embodiment, when the composition contains the oxidizing agent and the basifying agent, then the composition according to the invention preferably contains more than 25% of fatty substances. According to this variant, the composition preferably contains more than 30% of fatty substances.

b) Nonionic Surfactants

The composition of the invention contains at least one nonionic surfactant chosen from alkyl(poly)glycosides, fatty acid esters of oxyalkylenated sorbitan and oxyalkylenated fatty alcohols.

Alkyl(poly)glycosides

The alkyl(poly)glycosides surfactants that may be used in the composition of the invention may be oxyalkylenated. These surfactants may be represented by formula (Ia) below:

$$R_1O-(R_2O)_t-(G)_v$$

in which:

$R_1$ represents a linear or branched alkyl or alkenyl radical comprising 6 to 24 carbon atoms and especially 8 to 18 carbon atoms, or an alkylphenyl radical whose linear or branched alkyl radical comprises 6 to 24 carbon atoms and especially 8 to 18 carbon atoms;

$R_2$ represents an alkylene radical comprising 2 to 4 carbon atoms,

G represents a sugar unit comprising 5 to 6 carbon atoms, t denotes a value ranging from 0 to 10 and preferably 0 to 4, v denotes a value ranging from 1 to 15 and preferably 1 to 4.

Preferably, the alkylpolyglycoside surfactants are compounds having the formula described above in which:

$R_1$ denotes a saturated or unsaturated, linear or branched alkyl radical comprising from 8 to 18 carbon atoms, $R_2$ represents an alkylene radical comprising 2 to 4 carbon atoms, t denotes a value ranging from 0 to 3, preferably equal to 0, G denotes glucose, fructose or galactose, preferably glucose;

the degree of polymerization, i.e. the value of v, may range from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkylpolyglycoside surfactant is an alkyl polyglucoside surfactant. C8/C16 alkyl-polyglycosides 1,4 are most particularly preferred, and especially decyl glucosides and caprylyl/capryl glucosides.

Among the commercial products, mention may be made of the products sold by the company Cognis under the names Plantaren® (600 CS/U, 1200 and 2000) or Plantacare® (818, 1200 and 2000); the products sold by the company SEPPIC under the names Oramix CG 110 and Oramix® NS 10; the products sold by the company BASF under the name Lutensol GD 70, or else the products sold by the company Chem Y under the name AG10 LK.

Preferably, use is made of $C_8/C_{16}$-alkyl polyglycosides 1,4, especially in an aqueous 53% solution, such as those sold by Cognis under the reference Plantacare® 818 UP.

Fatty Acid Ester of Oxyalkylenated Sorbitan

The nonionic surfactant(s) may be chosen from fatty acid esters of oxyalkylenated sorbitan, preferably of a saturated fatty acid. Preferably, the polyoxyalkylenated sorbitan ester is an ester of polyoxyethylenated sorbitan and of a C8-C14 saturated fatty acid. These surfactants are generally formed from an ester of a C8 to C14 fatty acid and of oxyethylenated sorbitan comprising from 2 to 50 oxyethylene units. Preferably, the polyoxyethylenated sorbitan esters of C8-C14 fatty acids are polyoxyethylenated sorbitan monoesters of C8-C14 fatty acids. Even more preferentially, the composition according to the invention comprises a lauric acid monoester of oxyethylenated sorbitan comprising from 2 to 10 oxyethylene units and preferably 4 oxyethylene units. According to this embodiment, the composition comprises sorbitan monolaurate oxyethylenated with 4 OE. This compound is also known under the name Polysorbate 21. It is sold, inter alia, under the name Tween 21 by the company Uniqema.

The ester of a C8 to C14 fatty acid and of oxyethylenated sorbitan comprising from 2 to 10 oxyethylene units may be used alone, or as a mixture with one or more other oxyethylenated derivatives of sorbitan.

Another fatty acid monoester of polyoxyalkylenated sorbitan may be a monoester of a C8 to C24 fatty acid and of oxyethylenated sorbitan comprising from 15 to 50 oxyethylene units.

According to this particular embodiment, the monoester is a monoester of a C8 to C24 fatty acid and of oxyethylenated sorbitan comprising 20 oxyethylene units, for example sorbitan monolaurate oxyethylenated with 20 OE.

Oxyalkylenated Fatty Alcohol

The nonionic surfactant(s) according to the invention may be chosen from oxyalkylenated fatty alcohols. For the purposes of the present invention, the term "oxyalkylenated fatty alcohol" means an oxyalkylenated alcohol containing a hydrocarbon-based chain comprising at least 6 carbon atoms. Preferably, the oxyalkylenated fatty alcohol is oxyethylenated. According to one embodiment, the fatty alcohol comprises at least 6 carbon atoms, and at least 2 oxyethylene (—OCH2—CH2—) units.

The oxyalkylenated fatty alcohol that is useful in the invention may be represented by formula (IIa) below:

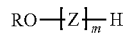

in which:

R denotes a saturated or unsaturated, linear or branched radical comprising from 6 to 40, in particular from 8 to 30 and preferably from 12 to 18 carbon atoms, and Z represents an oxyalkylenated, preferably oxyethylenated, radical, and m represents the number of ethylene oxide units ranging from 1 to 50, preferably 2 to 40 and better still 2 to 30.

As compounds of oxyethylenated fatty alcohol type, mention may be made especially of the following commercial products: Brij S2-SO-(SG) (Croda) [stearyl alcohol 2 OE]; Mergital LM2 (Cognis) [lauryl alcohol 2 OE]; Empilan KA 2.5/90FL (Albright & Wilson) and Mergital BL309 (Cognis) [decyl alcohol 3 OE]; Empilan KA 5/90 FL (Albright & Wilson) and Mergital BL589 (Cognis) [decyl alcohol 5 OE]; Emulgin 05 (Cognis) [oleocetyl alcohol 5 OE], Brij S20-PA-(SG) (Croda) [stearyl alcohol 20 OE]. Oxyethylenated fatty alcohols that are particularly preferred according to the invention are saturated or unsaturated, linear fatty alcohols comprising from 12 to 18 carbon atoms and from 2 to 30 oxyethylene units, in particular 2 to 20 ethylene oxide units. Preferably, the oxyethylenated fatty alcohol is a C16 and/or C18 fatty alcohol comprising from 2 to 20 oxyethylene units.

According to a particular embodiment, the polyoxyalkylenated, especially polyoxyethylenated, fatty alcohol is C12-C18, saturated and linear and comprises from 2 to 20 oxyethylene units.

Mention may be made especially of the adducts of ethylene oxide with lauryl alcohol, especially those comprising from 2 to 20 oxyethylene groups; the adducts of ethylene oxide with cetearyl alcohol (mixture of cetyl alcohol and stearyl alcohol), especially those comprising from 2 to 20 oxyethylene groups; the adducts of ethylene oxide with cetyl alcohol, especially those comprising from 2 to 20 oxyethylene groups; the adducts of ethylene oxide with stearyl alcohol, especially those comprising from 2 to 20 oxyethylene groups; the adducts of ethylene oxide with isostearyl alcohol, especially those comprising from 2 to 20 oxyethylene groups; the adducts of ethylene oxide with oleyl alcohol, especially those comprising from 2 to 20 oxyethylene groups; the adducts of ethylene oxide with isocetyl alcohol comprising from 2 to 20 oxyethylene groups, and mixtures thereof.

Preferably, the oxyethylenated fatty alcohol present in the composition according to the invention is chosen from stearyl alcohol comprising two ethylene oxide units or stearyl alcohol comprising 20 ethylene oxide units.

The nonionic surfactant(s) that are useful for the composition of the invention as described previously may be present in a content ranging from 0.1% to 30%, preferably from 0.5% to 20% and better still from 2% to 15% by weight relative to the total weight of the composition.

The composition for dyeing keratin fibres according to the invention may also contain one or more additional surfactants other than the nonionic surfactants as defined previously. According to a particular embodiment of the invention, the additional surfactant(s) are chosen from anionic, cationic and amphoteric surfactants.

c) 3-(2,5-Diaminophenyl)-1-propanol Oxidation Bases:

The composition of the invention comprises c) one or more oxidation bases chosen from 3-(2,5-diaminophenyl)-1-propanol (or 2-γ-hydroxypropyl-para-phenylenediamine) having the following formula, the acid salts thereof or the solvates thereof such as hydrates:

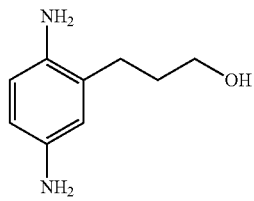 [SMILES: Nc1ccc(N)c(CCCO)c1]

The oxidation base(s) chosen from (2,5-diaminophenyl) propanol, the acid salts thereof or the solvates thereof such as hydrates, according to the invention, may be present in the composition of the invention in an amount ranging from 0.0001% to 20% by weight relative to the total weight of the composition, preferably from 0.005% to 10% by weight and more particularly from 0.01% to 10% by weight relative to the total weight of the composition.

The acid salts that may be used according to the invention may be chosen from hydrochlorides, hydrobromides, sulfates, citrates, succinates, tartrates, lactates, tosylates, benzenesulfonates, phosphates and acetates.

The composition according to the invention may comprise one or more additional oxidation bases other than 3-(2,5-diaminophenyl)-1-propanol, the acid salts thereof or the solvates thereof such as hydrates. According to a particular embodiment of the invention, the additional bases(s) are chosen from heterocyclic bases, benzene-based bases and the addition salts thereof or the solvates thereof.

As examples of additional benzene-based oxidation bases, mention may be made of para-phenylenediamines other than 3-(2,5-diaminophenyl)-1-propanol, bis(phenyl)alkylenediamines, para-aminophenols, ortho-aminophenols, and the addition salts thereof or solvates thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl) pyrrolidine, and the addition salts thereof with an acid, or the solvates thereof.

Among the para-phenylenediamines mentioned above, para-phenylenediamine or PPD, para-tolylenediamine or PTD, 2-isopropyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, or the solvates thereof, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof, or the solvates thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid, or the solvates thereof.

Among the ortho-aminophenols, examples that may be mentioned include 2-aminophenol, 2-amino-5-methylphenol, 2-amino-6-methylphenol, 5-acetamido-2-aminophenol and the addition salts thereof, or the solvates thereof.

The heterocyclic bases are more particularly chosen from pyridine derivatives, pyrimidine derivatives and pyrazole derivatives, and the addition salts thereof or solvates thereof.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof, or the solvates thereof.

Other pyridine oxidation bases that are useful in the dyeing process according to the invention are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-[(3-aminopyrazolo[1,5-a]pyridin-2-yl)oxy]ethanol, and the addition salts thereof, or the solvates thereof.

Among the pyrimidine derivatives, mention may be made of the compounds described, for example, in patents DE 2359399, JP 88-169571, JP 05-63124 and EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives mention may be made of the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. Use may also be made of 4,5-diamino-1-(β-methoxyethyl)pyrazole.

Use will preferably be made of a 4,5-diaminopyrazole and even more preferentially of 4,5-diamino-1-(β-hydroxyethyl)pyrazole and/or a salt or solvate thereof.

Pyrazole derivatives that may also be mentioned include diamino-N,N-dihydropyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt or solvate thereof.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or 2-(3-aminopyrazolo[1,5-a]pyridin-2-yloxy)ethanol and/or a salt or solvate thereof.

The additional oxidation base(s) according to the invention each advantageously represent from 0.0001% to 10% by weight relative to the total weight of the composition, and preferably from 0.005% to 5% by weight relative to the total weight of the composition.

d) Couplers

The composition of the invention comprises at least one coupler. Among these couplers, mention may be made especially of meta-phenylenediamines, meta-aminophenols, meta-diphenols, naphthalene-based couplers and heterocyclic couplers, and the addition salts or solvates thereof.

Examples that may be mentioned include 1,3-dihydroxybenzene, 1,3-dihydroxy-2-methylbenzene, 4-chloro-1,3-dihydroxybenzene, 1-hydroxy-3-aminobenzene, 2,4-diamino-1-(β-hydroxyethyloxy)benzene, 1-methyl-2-hydroxy-4-β-hydroxyethylamino benzene, 2-methyl-5-aminophenol, 5-amino-6-chloro-2-methylphenol, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methyl indole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid or the solvates thereof, and mixtures thereof.

The coupler(s) each advantageously represent from 0.0001% to 10% by weight relative to the total weight of the composition and preferably from 0.005% to 5% by weight relative to the total weight of the composition of the invention.

In general, the addition salts of the oxidation bases and couplers that may be used within the context of the invention are especially chosen from the addition salts with an acid such as the hydrochlorides, hydrobromides, sulfates, citrates, succinates, tartrates, lactates, tosylates, benzenesulfonates, phosphates and acetates.

Additional Dyes

The composition of the invention may also comprise one or more direct dyes. The latter dyes are more particularly chosen from ionic or nonionic species, preferably cationic or nonionic species. These direct dyes may be synthetic or of natural origin. When they are present, the direct dye(s) more particularly represent from 0.0001% to 10% by weight and preferably from 0.005% to 5% by weight relative to the total weight of the composition.

Basifying Agents:

The composition of the invention may also comprise one or more basifying agents. The basifying agent(s) may be mineral or organic or hybrid.

The mineral basifying agent(s) are preferably chosen from ammonia, alkali metal carbonates or bicarbonates such as sodium or potassium carbonates and sodium or potassium bicarbonates, sodium hydroxide or potassium hydroxide, or mixtures thereof.

The organic basifying agent(s) are preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise any alkyl or alkenyl fatty chain comprising more than ten carbon atoms.

The organic basifying agent(s) are chosen, for example, from alkanolamines, oxyethylenated and/or oxypropylenated ethylenediamines, amino acids and the compounds of formula (II) below:

in which formula (II) W is a divalent $C_1$-$C_6$ alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (II) that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Organic amines chosen from alkanolamines such as monoalkanolamines, dialkanolamines or trialkanolamines comprising one to three identical or different $C_1$-$C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that can be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that may be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

Preferably, the basifying agent(s) present in the composition of the invention are chosen from alkanolamines and amino acids in neutral or ionic form, in particular basic amino acids. According to a particularly preferred mode, the basifying agent(s) are chosen from monoethanolamine (MEA) and basic amino acids in neutral or ionic form.

Advantageously, the composition according to the invention has a content of basifying agent(s) ranging from 0.01% to 30% by weight and preferably from 0.1% to 20% by weight relative to the weight of the composition.

According to a first embodiment, the composition predominantly contains ammonia as basifying agent.

According to another embodiment, the composition contains ammonia and at least one other basifying agent, preferably chosen from alkanolamines. In this case, the composition comprises ammonia or a salt thereof, in an amount less than the amount of basifying agent(s) other than ammonia (expressed as $NH_3$). In particular, the composition contains little or no ammonia. Preferably, according to this embodiment, the ammonia content is less than or equal to 0.03% by weight (expressed as $NH_3$), preferably less than or equal to 0.01% by weight, relative to the weight of the composition of the invention. Preferably, the composition contains no ammonia.

Chemical Oxidizing Agent

The composition of the invention comprises one or more chemical oxidizing agents. The term "chemical oxidizing agent" means an oxidizing agent other than atmospheric oxygen. More particularly, the chemical oxidizing agent(s) are chosen from hydrogen peroxide, urea peroxide, alkali metal bromates, peroxygenated salts, for instance persulfates or perborates, peracids and precursors thereof and alkali metal or alkaline-earth metal percarbonates.

Advantageously, this oxidizing agent is hydrogen peroxide.

The concentration of chemical oxidizing agents may range more particularly from 0.1% to 50% by weight, even more preferentially from 0.5% to 20% by weight and better still from 1% to 15% by weight relative to the weight of the composition.

Preferably, the composition of the invention does not contain any peroxygenated salts.

Solvent

The composition according to the invention may also comprise one or more organic solvents.

Examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether and monoethyl ether, and also aromatic alcohols or ethers, for instance benzyl alcohol or phenoxyethanol, and mixtures thereof.

The solvent(s), if they are present, represent a content usually ranging from 1% to 40% by weight and preferably from 5% to 30% by weight relative to the weight of the composition.

Other Ingredients

The composition according to the invention may also contain various ingredients conventionally used in hair dye compositions, such as anionic, cationic, nonionic, amphoteric or zwitterionic polymers or mixtures thereof; mineral thickeners, and in particular fillers such as clays or talc; organic thickeners with, in particular, anionic, cationic, nonionic and amphoteric polymeric associative thickeners; antioxidants; penetrants; sequestrants; fragrances; dispersants; film-forming agents; ceramides; preserving agents; opacifiers.

The above ingredients are generally present in an amount, for each of them, of between 0.01% and 20% by weight, relative to the weight of the composition. The composition of the invention may be in various forms, for instance a solution, an emulsion (milk or cream) or a gel, preferably in the form of an emulsion.

Processes of the Invention

The composition according to the invention is applied to wet or dry keratin fibres. It is left in place on the fibres for a time generally of from 1 minute to 1 hour and preferably from 5 minutes to 30 minutes. According to a preferred embodiment, the composition applied contains at least one basifying agent and at least one oxidizing agent.

The temperature during the dyeing process is conventionally between room temperature (between 15° C. and 25° C.) and 80° C. and preferably between room temperature and 60° C.

After the treatment, the human keratin fibres are optionally rinsed with water, optionally washed with a shampoo and then rinsed with water, before being dried or left to dry.

According to a preferred embodiment, the composition according to the invention is prepared by mixing at least two compositions, a first composition (A) which comprises the oxidation base 3-(2,5-diaminophenyl)-1-propanol and/or an acid salt or solvate thereof and a second composition (B) which comprises at least one chemical oxidizing agent, it being understood that:

at least one of the compositions (A) or (B) comprises the fatty substance(s) and the nonionic surfactant(s) of use for the invention and as defined previously such that the fatty substance content of the composition resulting from the mixing of compositions (A)+(B) is at least 10%, preferably greater than 25%, preferably greater than 30% by weight, relative to the weight of the composition derived from the mixing of (A)+(B).

According to one embodiment, at least one of the compositions (A) or (B) is aqueous, and preferentially both compositions (A) and (B) are aqueous.

The term "aqueous composition" means a composition comprising at least 5% water. Preferably, an aqueous composition comprises more than 10% by weight of water and more advantageously still more than 20% by weight of water.

In one variant of the invention, at least part of the fatty substance(s) is present in a third composition which is mixed with compositions (A) and (B) under the conditions defined above. Preferably, this third composition is anhydrous.

More particularly, for the purposes of the invention, the expression "anhydrous cosmetic composition" means a cosmetic composition with a water content of less than 5% by weight, preferably less than 2% by weight and more preferably still less than 1% by weight relative to the weight of said composition. It should be noted that the water present in the composition is more particularly "bound water", such as water of crystallization in salts, or traces of water absorbed by the starting materials used in the preparation of the compositions according to the invention.

The examples that follow serve to illustrate the invention without, however, being limiting in nature.

EXAMPLES

Example 1

The following compositions are prepared in which the amounts are expressed in grams of active materials.

Dye compositions (g %)

| Ingredients | A | B |
|---|---|---|
| Sodium metabisulfite in powder form | 0.45 | 0.45 |
| Pure monoethanolamine | 4.57 | 4.65 |
| Ethylenediaminetetraacetic acid | 0.2 | 0.2 |
| 6-Hydroxybenzomorpholine | — | 0.04 |
| 1-β-Hydroxyethyloxy-2,4-diaminobenzene dihydrochloride | — | 0.16 |
| 2-Methyl-1,3-dihydroxybenzene (2-methylresorcinol) | 0.17 | — |
| N,N-Bis(2-hydroxyethyl)-p-phenylenediamine sulfate monohydrate | — | 0.13 |

-continued

| Ingredients | A | B |
|---|---|---|
| 1,3-Dihydroxybenzene (resorcinol) | 0.2 | 1 |
| 1-Hydroxy-3-aminobenzene | 0.025 | 0.16 |
| 3-(2,5-Diaminophenyl)propan-1-ol hydrochloride | 0.75 | 2.83 |
| Mineral oil (INCI name) | 60 | 60 |
| Perfume | 0.72 | 0.72 |
| Cationic hydroxyethylcellulose (Polyquaternium-67) marketed under the name Softcat Polymer SL-100 by Dow Chemical | 0.19 | 0.19 |
| water | Qs 100 | Qs 100 |
| Oxyethylenated stearyl alcohol (2 OE) | 1.13 | 1.13 |
| Oxyethylenated stearyl alcohol (20 OE) | 3.88 | 3.88 |
| Caprylyl/capryl glucoside (alkyl (C8/C10 50/50) polyglucoside (2) in 60% buffered aqueous solution) | 2.4 | 2.4 |
| Oxyethylenated sorbitan monolaurate (4 OE) | 2.4 | 2.4 |
| Vitamin C: ascorbic acid | 0.25 | 0.25 |

Oxidizing composition C (g % of active material)

| Ingredients | C |
|---|---|
| Pentasodium pentetate | 0.06 |
| Hydrogen peroxide | 6 |
| Sodium stannate | 0.04 |
| Phosphoric acid | qs pH = 2.2 |
| Tetrasodium pyrophosphate | 0.03 |
| Mineral oil | 20 |
| Hexadimethrine chloride | 0.15 |
| Polyquaternium-6 | 0.2 |
| Water | qs 100 |
| Glycerol | 0.5 |
| Cetearyl alcohol | 6 |
| Steareth-20 | 5 |
| PEG-4 Rapeseedamide | 1.2 |
| Tocopherol | 0.1 |

At the time of use, each of the compositions A and B is mixed with one time its own weight of oxidizing composition C.

The mixtures thus obtained are applied to natural hair containing 90% white hairs.

After a leave-on time of 35 minutes at room temperature, the hair is rinsed and washed with a standard shampoo, then dried. An attractive Blonde shade is obtained with formula A and a Chestnut shade is obtained with formula B.

Example 2

The following compositions have been prepared in which the amounts are expressed in grams of active materials.

| | B' invention | B" comparative |
|---|---|---|
| Sodium metabisulfite | 0.45 | 0.45 |
| Monoethanolamine | 4 | 4 |
| Ethylenediaminetetraacetic acid | 0.2 | 0.2 |
| 6-HYDROXY BENZOMORPHOLINE | 0.04 | 0.04 |
| 1-BETA-HYDROXYETHYLOXY-2,4-DIAMINOBENZENE 2 Hcl | 0.16 | 0.16 |
| 2-METHYL-1,3-DIHYDROXYBENZENE (2-METHYL RESORCINOL) | 0.17 | 0.17 |
| Para aminophenol | 0.13 | 0.13 |
| 1,3-DIHYDROXYBENZENE (RESORCINOL) | 0.21 | 0.21 |
| 1-HYDROXY-3-AMINO-BENZENE | 0.16 | 0.16 |
| 3-(2,5-DIAMINOPHENYL)PROPAN-1-OL HCl | $4.18 \times 10^{-3}$ mol | — |
| 2-b hydroxyethyl para phenylenediamine | — | $4.18 \times 10^{-3}$ mol |
| MINERAL OIL | 60 | 60 |
| PERFUME | 0.72 | 0.72 |
| Cationic Hydroxyethylcellulose (Polyquaternium-67) SOFTCAT SL-100 | 0.19 am* | 0.19 am |
| WATER | qs | qs |
| Oxyethylenated stearyl alcohol (2 OE) | 1.13 | 1.13 |
| Oxyethylenated stearyl alcohol (20 OE) | 3.88 | 3.88 |
| (50/50 $C_8/C_{10}$) Alkyl (2)-polyglucoside as a 60% aqueous solution (Oramix CG 110 from SEPPIC) | 2.4 am | 2.4 am |
| Oxyethylenated sorbitan monolaurate (4 OE) | 2.4 | 2.4 |
| Vitamin C | 0.25 | 0.25 |

*Active material

At the time of use, each composition B' and B" is mixed with the oxidizing composition C of example 1 at a weight ratio of 1/1.

The resulting mixture are each applied on natural hair locks (BN), which represents the hair root, and permed hair locks (BP), which represents the hair tips, in an amount of 10 g of composition per 1 g of hair, and left for 35 minutes at room temperature (25° C.).

Then the hair was rinsed with water, washed with the "Pro Classics concentrated" shampoo (L'Oréal Professionnel), diluted at 10%, and dried.

Selectivity Evaluation

The color of the hair was determined using the CIE L*a*b* system with a Minolta CM2006D spectrophotometer (illuminant D65, angle 10°, specular component included) in the CIELab system.

According to this system, L* indicates the lightness of the color of the hair. The chromaticity coordinates are expressed by the parameters a* and b*, a* indicating the axis of red/green shades and b* the axis of yellow/blue shades.

The selectivity of the dyeing is measured by calculating the variation of ΔE according to the formula:

$$\Delta E = \sqrt{(L^*-L_o^*)^2+(a^*-a_o^*)^2+(b^*-b_o^*)^2}$$

In which L, a* and b* represent the values measured on natural hair and L0*, a0* and b0* represent the values measured on permed hair.

The selectivity is represented by the difference of color between the colored natural hair and permed hair: the more is the ΔE value, the more the difference of color between natural and permed hair is important, which is representative of the homogeneity of the coloration between the roots and the tips along the lock of hair.

The following results are obtained:

| | Hair type | L* | a* | b* | ΔE |
|---|---|---|---|---|---|
| B' + C (invention) | BN | 22.14 | 1.16 | 0.36 | 3.85 |
| | BP | 18.39 | 0.54 | −0.24 | |
| B" + C (comparative) | BN | 26.24 | 2.18 | 2.04 | 5.94 |
| | BP | 20.64 | 1.28 | 0.28 | |

The mixtures B'+C according to the invention provide less selective colorations (lower ΔE value) than the mixture of compositions B"+C (comparative):the difference between the raw and the tips is lower with B'+C than with B"+C: the coloration along the lock of hair is more homogenous with B'+C.

The invention claimed is:

1. A composition comprising:
   a) at least one oxidation base chosen from 3-(2,5-diaminophenyl)-1-propanol, acid salts thereof, or solvates thereof;
   b) at least one coupler;
   c) at least one fatty substance, wherein the total amount of fatty substance is at least about 10% by weight, relative to the total weight of the composition;
   d) at least one nonionic surfactant chosen from alkyl (poly)glycoside surfactants, fatty acid esters of oxyalkylenated sorbitan, or oxyalkylenated fatty alcohols;
   e) optionally at least one basifying agent; and
   f) optionally at least one chemical oxidizing agent.

2. The composition according to claim 1, wherein the at least one fatty substance is chosen from $C_6$-$C_{16}$ hydrocarbons, hydrocarbons containing more than 16 carbon atoms, non-silicone oils of animal origin, plant oils of triglyceride type, synthetic triglycerides, fluoro oils, fatty alcohols, esters of fatty acids and/or of fatty alcohols other than triglycerides and plant waxes, non-silicone waxes, and silicones.

3. The composition according to claim 1, wherein the at least one fatty substance is liquid at room temperature and at atmospheric pressure.

4. The composition according to claim 1, wherein the at least one fatty substance is chosen from $C_6$-$C_{16}$ hydrocarbons, hydrocarbons containing more than 16 carbon atoms, triglycerides, fatty alcohols, esters of fatty acids and/or of fatty alcohols other than triglycerides, or mixtures thereof.

5. The composition according to claim 1, wherein the total amount of fatty substance ranges from about 15% to about 80% by weight, relative to the total weight of the composition.

6. The composition according to claim 1, wherein the at least one nonionic surfactant is chosen from alkylpolyglycosides according to formula (Ia) below:

wherein:
   $R_1$ is chosen from a linear or branched alkyl or alkenyl radical comprising 6 to 24 carbon atoms, or an alkylphenyl radical whose linear or branched alkyl radical comprises 6 to 24 carbon atoms;
   $R_2$ is an alkylene radical comprising 2 to 4 carbon atoms;
   G is a sugar unit comprising 5 to 6 carbon atoms;
   t is an integer ranging from 0 to 10; and
   v is an integer ranging from 1 to 15.

7. The composition according to claim 6, wherein in formula (Ia):
   $R_1$ is a saturated or unsaturated, linear or branched alkyl radical comprising from 8 to 18 carbon atoms;
   $R_2$ is an alkylene radical comprising 2 to 4 carbon atoms;
   G is chosen from glucose, fructose, or galactose;
   t is an integer ranging from 0 to 3; and
   v is an integer ranging from 1 to 15.

8. The composition according to claim 1, wherein the at least one nonionic surfactant is chosen from fatty acid esters of oxyalkylenated sorbitan.

9. The composition according to claim 8, wherein the fatty acid esters of oxyalkylenated sorbitan are chosen from esters of polyoxyethylenated sorbitan and of a $C_8$-$C_{14}$ saturated fatty acid.

10. The composition according to claim 1, wherein the at least one nonionic surfactant is chosen from oxyalkylenated fatty alcohols according to formula (IIa) below:

wherein:
   R is chosen from a saturated or unsaturated, linear or branched radical comprising from 6 to 40 carbon atoms;
   Z is an oxyethylenated radical; and
   m is the number of ethylene oxide units ranging from 1 to 50.

11. The composition according to claim 1, wherein the at least one nonionic surfactant is chosen from $C_{16}$-$C_{18}$ polyoxyethylenated fatty alcohols comprising from 2 to 20 oxyethylene units.

12. The composition according to claim 1, wherein the total amount of nonionic surfactant ranges from about 0.1% to about 30%, relative to the total weight of the composition.

13. The composition according to claim 1, wherein the amount of the at least one oxidation base chosen from 3-(2,5-diaminophenyl)-1-propanol, acid salts thereof, or solvates thereof ranges from about 0.0001% to about 20% by weight, relative to the total weight of the composition.

14. The composition according to claim 1, wherein the at least one coupler is chosen from meta-phenylenediamines, meta-aminophenols, meta-diphenols, naphthalene-based couplers and heterocyclic couplers, or addition salts thereof.

15. The composition according to claim 1, comprising the at least one basifying agent chosen from ammonia, alkali metal carbonates or bicarbonates, sodium hydroxide or potassium hydroxide, organic amines, amino acids, or the compounds corresponding to formula (II), or mixtures thereof:

wherein:
   W is chosen from a divalent $C_1$-$C_6$ alkylene radical optionally substituted with at least one hydroxyl group or a $C_1$-$C_6$ alkyl radical, and/or optionally interrupted with at least one heteroatom chosen from 0 or $NR_u$; and
   $R_x$, $R_y$, $R_z$, $R_t$, and $R_u$ are independently chosen from hydrogen, a $C_1$-$C_6$ alkyl, a $C_1$-$C_6$ hydroxyalkyl, or $C_1$-$C_6$ aminoalkyl radical.

16. The composition according to claim 15, wherein the basifying agent is chosen from ammonia or alkanolamines, or neutral or ionic amino acids.

17. The composition according to claim 1, comprising the at least one chemical oxidizing agent.

18. A process for dyeing keratin fibers comprising applying to the keratin fibers a composition comprising:
   a) at least one oxidation base chosen from 3-(2,5-diaminophenyl)-1-propanol, acid salts thereof, or solvates thereof;
   b) at least one coupler;
   c) at least one fatty substance, wherein the total amount of fatty substance is at least about 10% by weight, relative to the total weight of the composition;

d) at least one nonionic surfactant chosen from alkyl (poly)glycoside surfactants, fatty acid esters of oxyalkylenated sorbitan, or oxyalkylenated fatty alcohols;
e) optionally at least one basifying agent; and
f) optionally at least one chemical oxidizing agent.

19. The process of claim 18, wherein the composition applied to the keratin fibers is obtained by mixing:
 a first composition (A) comprising at least one oxidation base chosen from 3-(2,5-diaminophenyl)-1-propanol, acid salts thereof, or solvates thereof; and
 a second composition (B) comprising at least one chemical oxidizing agent;
  wherein at least one of the compositions (A) or (B) comprises at least one fatty substance and at least one nonionic surfactant, in the same or different compositions; and
  wherein the total amount of fatty substance in the composition resulting from the mixing of compositions (A) and (B) is at least about 10%, relative to the weight of the composition obtained from the mixing of (A) and (B).

20. The process of claim 19, wherein the composition applied to the keratin fibers is obtained by mixing:
 a first composition (A) comprising at least one oxidation base;
 a second composition (B) comprising at least one chemical oxidizing agent; and
 a third composition comprising at least one fatty substance;
  wherein at least one of the compositions (A) or (B) comprises at least one fatty substance and at least one nonionic surfactant, in the same or different compositions;
  wherein the fatty substance in compositions (A) or (B) is the same or different than the fatty substance it the third composition; and
  wherein the total amount of fatty substance in the composition resulting from the mixing of the first composition (A), the second composition (B), and the third composition is at least about 10%, relative to the weight of the composition obtained from the mixing of the first composition (A), the second composition (B), and the third composition.

21. A multi-compartment device comprising:
 a first compartment containing composition (A) comprising at least one oxidation base chosen from 3-(2,5-diaminophenyl)-1-propanol and/or one of acid salts or solvates; and
 a second compartment containing composition (B) comprising at least one chemical oxidizing agent;
  wherein at least one of the compositions (A) or (B) comprises at least one fatty substance and the at least one nonionic surfactant;
 wherein the total amount of fatty substance in the composition resulting from the mixing of compositions (A) and (B) is at least about 10%, relative to the weight of the composition obtained from the mixing of (A) and (B).

* * * * *